(12) United States Patent
Allier et al.

(10) Patent No.: US 10,132,737 B2
(45) Date of Patent: Nov. 20, 2018

(54) METHOD AND SYSTEM FOR CHARACTERIZING A STATE OF ADHESION OF PARTICLES SUCH AS CELLS

(71) Applicant: COMMISSARIAT A L'ENERGIE ATOMIQUE ET AUX ENERGIES ALTERNATIVES, Paris (FR)

(72) Inventors: Cedric Allier, Grenoble (FR); Srikanth Vinjimore Kesavan, Fontaine (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/122,190

(22) PCT Filed: Mar. 5, 2015

(86) PCT No.: PCT/EP2015/054669
§ 371 (c)(1),
(2) Date: Aug. 29, 2016

(87) PCT Pub. No.: WO2015/132360
PCT Pub. Date: Sep. 11, 2015

(65) Prior Publication Data
US 2016/0370283 A1  Dec. 22, 2016

(30) Foreign Application Priority Data
Mar. 5, 2014 (FR) ...................... 14 51785

(51) Int. Cl.
*G01N 21/00* (2006.01)
*G01N 15/14* (2006.01)
(Continued)

(52) U.S. Cl.
CPC ......... *G01N 15/1463* (2013.01); *G01N 15/14* (2013.01); *G01N 21/4788* (2013.01);
(Continued)

(58) Field of Classification Search
CPC .... G01N 15/14; G01N 15/1463; G01N 21/47; G01N 21/4788; G02B 27/42;
(Continued)

(56) References Cited

U.S. PATENT DOCUMENTS

2007/0042483 A1\* 2/2007 Bornens ............... C12N 5/0068
435/177
2014/0376816 A1\* 12/2014 Lagae ................ G01N 15/1436
382/195

OTHER PUBLICATIONS

C. P. Allier et al ; "Video lensfree microscopy of 2D and 3D culture of cells", Proc. SPIE 8947, Imaging, Manipulation, and Analysis of Biomolecules, Cells, and Tissues XII, 89471H (Mar. 4, 2014).\*
(Continued)

*Primary Examiner* — Jamil Ahmed
(74) *Attorney, Agent, or Firm* — Young & Thompson (57) ABSTRACT

This method for characterizing a state of adhesion of the particles is applied via a system including a source of spatially coherent light and a photodetector array, the particles being contained in a liquid medium, the liquid medium being delimited by a transparent surface, the particles being able to adhere to the transparent surface. The method includes: illuminating the medium with the source of spatially coherent light; acquiring at least one image by the photodetector array, the image being formed by radiation transmitted by the illuminated medium and including at least one elementary diffraction pattern, each elementary diffraction pattern corresponding to waves diffracted by a particle during the illumination of the medium; and computing, from at least one acquired image and for at least one particle, a primary indicator characterizing the state of adhesion of the particle to the transparent surface.

13 Claims, 6 Drawing Sheets

(51) Int. Cl.
*G01N 21/47* (2006.01)
*G03H 1/08* (2006.01)
*G02B 27/42* (2006.01)
*G03H 1/00* (2006.01)
*G03H 1/04* (2006.01)

(52) U.S. Cl.
CPC ....... *G02B 27/4205* (2013.01); *G03H 1/0005* (2013.01); *G03H 1/0443* (2013.01); *G03H 1/0808* (2013.01); *G03H 1/0866* (2013.01); *G03H 2001/0033* (2013.01); *G03H 2001/0447* (2013.01)

(58) Field of Classification Search
CPC ........ G02B 27/4205; G03H 1/00; G03H 1/08; G03H 1/22; G03H 1/0005; G03H 1/0443; G03H 1/0808; G03H 1/0866; G03H 2001/0033; G03H 2001/0447; G06T 7/00; G06K 9/46
See application file for complete search history.

(56) References Cited

OTHER PUBLICATIONS

French Preliminary Search Report, dated Oct. 28, 2014, from corresponding PCT application.

International Search Report, dated May 15, 2015, from corresponding PCT application.

S. Vinjimore Kesavan et al., Lensless imaging system to quantify cell proliferation, Proceedings of SPIE, Feb. 22, 2013, vol. 8587, p. 858708.

S. Paschalakis et al., "Pattern Recognition in grey level images using moment based invariant features", Image Processing and Its Applications, Jul. 13, 1999, vol. 1, pp. 245-249.

S. Vinjimore Kesavan et al., "Multi-scale high-throughput cell culture monitoring by lensfree imaging", Sep. 21, 2013, Retrieved from internet: URL:http://www.wmis.org/abstracts/2013/data/papers/SS166.htm.

Geonsoo Jin et al., "Lens-free shadow image based high-throughput continuous cell monitoring technique", Biosensors and Bioelectronics, May 9, 2012, pp. 126-131, vol. 38, No. 1.

C.P. Allier et al., "Video lensfree microscopy of 2D and 3D cultures of cells", Progress in Biomedical Optics and Imaging, SPIE, Mar. 4, 2014, p. 89471H, vol. 8947.

Monika E. Dolega et al., "Label-free analysis of prostate acini-like 3D structures by lensfree imaging", Biosensors and Bioelectronics, May 21, 2013, pp. 176-183, vol. 49.

Vijaykrishna Ragunathan et al, "Influence of Extracellular Matrix Proteins and Substratum Topography on Corneal Epithelial Cell Alignment and Migration", Tissue Engineering Part A, Mar. 14, 2013, pp. 1713-1722, vol. 19, Nos. 15-16.

* cited by examiner

METHOD AND SYSTEM FOR CHARACTERIZING A STATE OF ADHESION OF PARTICLES SUCH AS CELLS

FIELD OF THE INVENTION

The present invention relates to a method for characterizing a state of adhesion of at least one particle. The particle(s), such as cells, are contained in a liquid medium, the liquid medium being delimited by a transparent surface, and the particles are able to adhere to said transparent surface.

The invention also relates to a system for characterizing the state of adhesion of said particle(s) to said transparent surface.

BACKGROUND OF THE INVENTION

The cell adhesion is generally classified according to two categories, i.e. a first category relative to the adhesion between a cell and a substrate and a second category relative to the adhesion between two cells. The present invention relates to the first category of cell adhesion cellular between the cell and the substrate.

Most cells are adherent to a substrate, except for a few exceptions like hematopoietic cells for example. Adhesion of a cell to a substrate is a complex process involving diverse proteins. In addition to diverse other functions such as metastasis, healing of wounds, differentiation of tissues, the adhesion of a cell to a substrate forms a communication means between the cell and its environment. This communication is required for migration and proliferation of the cells. Incapability of the cells of adhering to the substrate may lead to their death.

Studying the adhesion of the cell to the substrate is therefore important for analyzing the fundamental processes associated with the cell. Such a study may provide an answer to questions concerning the relationships between the structure and function of cell adherence molecules and their respective ligands. Such a study is moreover able to provide information on the connection between the individual adhesive properties of cells and their capability of acting in a multi-cell environment, upon examining processes such as growth, angiogenesis, invasion, extravasation, metastasis, synthesis of proteins of the matrix or further secretion of degradation enzymes. Studying the adhesion of the cell to the substrate is finally a useful tool in the screening of reagents which interfere with cell adhesion to substrates, or further promotes it, as this was described in the article "Enzymatic quantification of cell-matrix and cell-cell adhesion", of Löster et al., published in the journal Micron, Volume 31, Number 1, pages 41 to 53, in January 2000.

Different techniques for studying the adhesion of the cell to the substrate have been described in the aforementioned article, in the article "Cell adhesion assays" of M. J. Humphries, published in the journal Methods in molecular biology, Volume 522, pages 203 to 210, in January 2009, as well as in the article "Heterotypic Cell Adhesion Assay for the Study of Cell Adhesion Inhibition" of Satyanarayanajois et al., published in the journal Drug Design and Discovery.

These techniques involve different handling operations, typically additions of reagents in the liquid, followed by multiple washes and multiple optical acquisitions (microscopy, cytometry, optical density). In fact, they are costly in reagents and in manpower time and remain difficult to apply. In particular, they strongly depend on the efficiency of the reagent. More importantly, they do not allow or only with difficulty the carrying out of measurements continuously over time. Further, they do not give the possibility of following individually thousands of cells which reduces the statistical quality of the measurement, beyond the use of a marker and/or of a reagent which may interfere with the life of the cell which biases the measurement. In the worst case, the method is destructive of the sample: the fluorescent marking associated with a cytometry measurement is destructive for the sample.

SUMMARY OF THE INVENTION

The object of the invention is therefore to propose a method and a system for characterizing a state of adhesion of at least one particle to a substrate which are less costly, easier to apply. From an experimental point of view, the invention then gives the possibility of carrying out a continuous measurement of the cell adhesion, of tracking in parallel thousands of cells with a single measurement per cell and of not requiring any marking or reagent.

For this purpose, the subject-matter of the invention is a method for characterizing a state of adhesion of at least one particle, via a system comprising a source of spatially coherent light and a photodetector array, the particle(s), such as cells, being contained in a liquid medium, the liquid medium being delimited by a transparent surface, the particle(s) being able to adhere to said transparent surface, the method comprising:
  illuminating the medium with the spatially coherent light source,
  acquiring at least one image with the photodetector array, the image being formed by radiation transmitted through the illuminated medium and including at least one elementary diffraction pattern, each elementary diffraction pattern corresponding to waves diffracted by one particle during the illumination of the medium, and
  computing, from at least one acquired image and for at least one particle, a primary indicator characterizing the state of adhesion of the particle to the transparent surface.

According to other advantageous aspects of the invention, the characterization method comprises one or several of the following features, taken individually or according to all the technically possible combinations:
  the photodetector array is able to measure the intensity of at least one diffraction pattern, and the calculated primary indicator depends on the intensity at the center of a corresponding diffraction pattern;
  a particle is determined as being adherent when the value of said primary indicator exceeds a threshold;
  computing each primary indicator includes the localization, on the acquired image, of the center of each elementary diffraction pattern corresponding to a predetermined pattern;
  computing each primary indicator includes the localization, on the acquired image, of the center of an elementary diffraction pattern, this localization being achieved from:
    a reconstruction of an image of the particle associated with said elementary diffraction pattern, by applying a reconstruction algorithm, and then
    the detection in the reconstructed image, of the position corresponding to the center of said elementary diffraction pattern;
  the method further comprises the definition of a region of interest around the center of each elementary diffraction pattern;

the method further comprises computing, from at least one acquired image and for at least one particle, at least one secondary indicator characterizing the spreading of a cell having adhered to the transparent surface, each secondary indicator being distinct from the primary indicator;

the photodetector array is able to measure the distribution of the intensity of at least one diffraction pattern, and at least one calculated secondary indicator depends on a moment of order M of the intensity at the center of a corresponding diffraction pattern, M being an integer with a value greater than or equal to 3;

the method further comprises computing the time derivative of at least one calculated secondary indicator for detecting the spreading of the cell having adhered to the transparent surface;

a first calculated secondary indicator depends on the moment of order 3 of the intensity at the center of the corresponding diffraction pattern;

computing each first secondary indicator includes the determination of a region of interest of the acquired image including the corresponding diffraction pattern, and each first secondary indicator verifies the following equation:

$$S = E\left[\left(\frac{X-\mu}{\sigma}\right)^3\right]$$

where X represents the distribution of the intensity of said determined region of interest, $\mu$ represents the quadratic average of the intensity of the determined region, and $\sigma$ represents the standard-deviation of the intensity of the determined region;

a second calculated secondary indicator depends on the moment of order 4 of the intensity at the center of the corresponding region of interest;

computing each second secondary indicator includes the determination of a region of the acquired image including the corresponding diffraction pattern, and each second secondary indicator verifies the following equation:

$$K = E\left[\left(\frac{X-\mu}{\sigma}\right)^4\right]$$

where X represents the distribution of the intensity of said determined region of interest, $\mu$ represents the quadratic average of the intensity of the determined region of interest, and $\sigma$ represents the standard-deviation of the intensity of the determined region of interest.

The subject-matter of the invention is also a system for characterizing a state of adhesion of at least one particle, the particle(s), such as cells, being contained in a liquid medium, the liquid medium being delimited by a transparent surface, the particle(s) being able to adhere to said transparent surface, the system comprising:

a source of spatially coherent light able to emit a light beam for illuminating the liquid medium, a photodetector array able to acquire at least one image of radiation transmitted through the illuminated medium, the image including at least one diffraction pattern, each diffraction pattern corresponding to waves diffracted by a particle of the illuminated medium, and an information processing unit including a first computing module for computing, from at least one acquired image and et for at least one particle, a primary indicator characterizing the sate of adhesion of the particle to the transparent surface.

BRIEF DESCRIPTION OF THE DRAWINGS

The features and the advantages of the invention will become apparent upon reading the description which follows, only given as a non-limiting example, and made with reference to the appended drawings, wherein.

DESCRIPTION OF PREFERRED EMBODIMENTS

In the following of the description, the expression «substantially equal to» defines an equality relationship to within plus or minus 5%.

Figure 1:
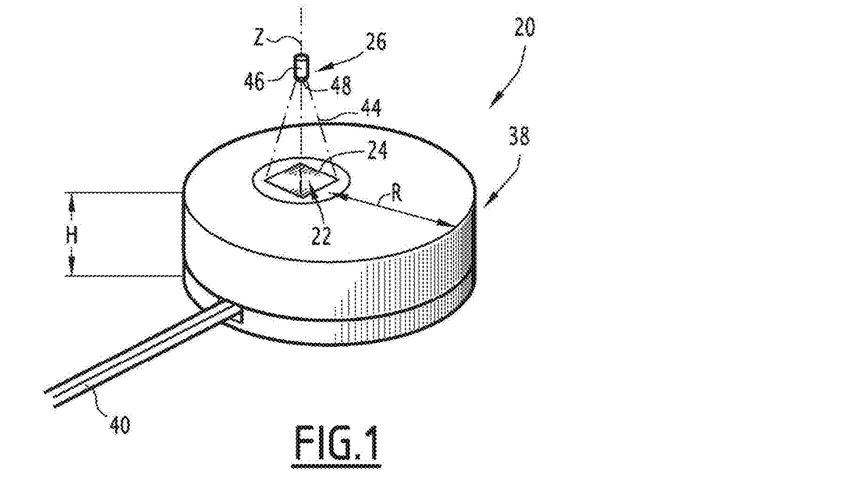
FIG. 1 is a perspective view of characterization system according to the invention.
Figure 2:
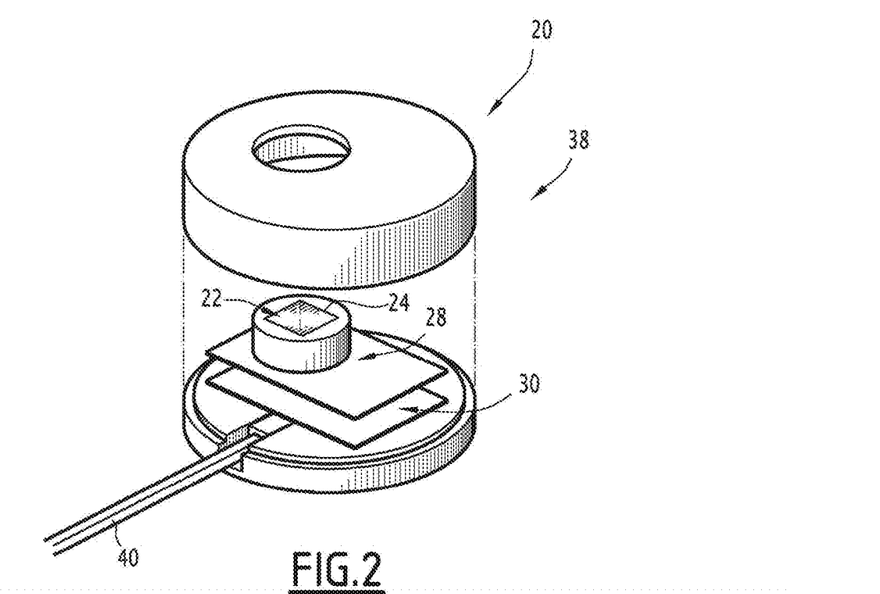
FIG. 2 is an exploded view of the characterization system of FIG. 1.

In FIGS. 1 and 2, a system 20 for characterizing a state of adhesion of particles 22 contained in a liquid medium 24, comprises a source of spatially coherent light 26 and a photodetector array 28 able to acquire at least one image of radiation transmitted through the illuminated medium 24 by the light source 26. The liquid medium 24 is delimited by a transparent surface 29, visible in FIG. 3, and the state of adhesion characterized by the characterization system 20 is the state of adhesion of the particles 22 to the transparent surface 29.

Figure 3:
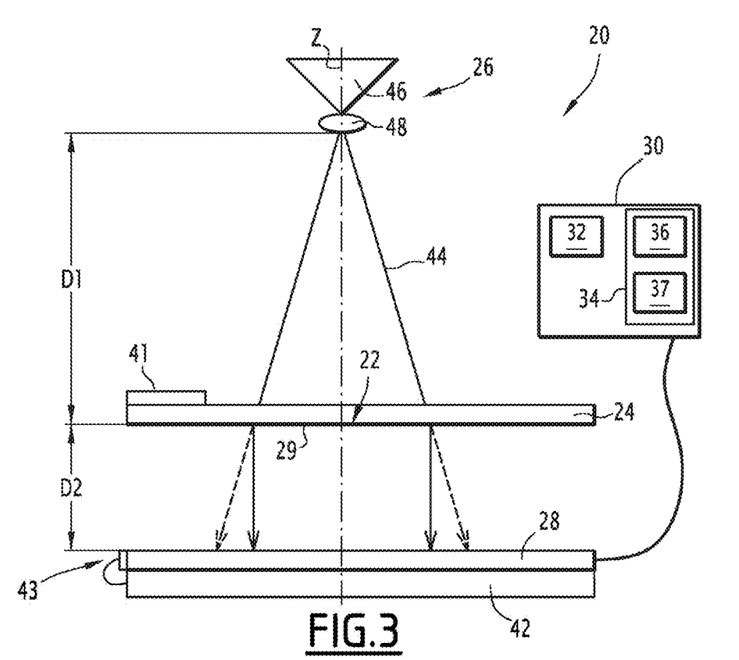
FIG. 3 is a schematic illustration of the characterization system of FIG. 1, the characterization system comprising a light source, a photodetector array, and an information processing unit including a first computing module for computing a primary indicator characterizing the state of adhesion of a corresponding particle, such as a cell, to the transparent surface and a second computing module for computing at least one secondary indicator characterizing the spreading of the cell having adhered to the transparent surface, each secondary indicator being distinct from the primary indicator, FIG. 4 s a flowchart of a characterization method according to the invention.

The characterization system 20 also comprises an information processing unit 30, visible in FIG. 3, including a processor 32 and a memory 34. The memory 34 is able to store a first computing module such as a first computing software 36, from at least one acquired image and for at least one particle 22, of a primary indicator characterizing the state of adhesion of the particle 22 to the transparent surface 29. Additionally, the memory 34 is able to store a second computing module such as a second computing software 37, from at least one acquired image and for at least one particle 22, of at least one secondary indicator S, K characterizing the spreading of a cell 22 having adhered to the transparent surface 29, each secondary indicator S, K being distinct from the primary indicator.

Alternatively, the first computing module and the second computing module are made as programmable logic components or further as dedicated integrated circuits.

Thus, generally, the characterization system 20 is intended to characterize the adhesion or not of a given particle 22, such as a cell, to the transparent surface 29, and if necessary to further characterize the spreading of a cell 22 having adhered to the transparent surface 29. The characterization system 20 is then able to characterize the adhesion of the particle 22 to the transparent surface 29 when said particle 22 moves towards this surface, but also the detachment of a particle 22 relatively to the surface 29 to which the particle has adhered beforehand. The adhesion of the particle 22 corresponds to the moment when the particle 22 is set on the surface 29 or further to the moment when the particle 22 is in contact with said surface 29 and adheres thereto.

The characterization system 20 comprises a protective casing 38, visible in FIGS. 1 and 2, inside which are notably positioned the photodetector 28 and the information processing unit 30. The characterization system 20 comprises a wire connection 40 of an electric power supply.

Additionally, the characterization system 20 comprises a heat source 41 such as a heating resistor, visible in FIG. 3, in order to avoid any condensation on an optional protective lid of the liquid medium 24, this in order not to perturb the acquisition of the images with the photodetector array 28. The heat source 41 is for example positioned inside the protective casing 38.

Still additionally, the characterization system 20 comprises a module 42 for regulating temperature, coupled with a temperature probe 43, as illustrated in FIG. 3. The temperature regulating module 42 allows regulation of the temperature of the photodetector array 28 at a predetermined temperature, for example 37° Celsius, in order not to perturb proper cell growth. The temperature regulating module 42 is for example a module of the Peltier type and the temperature probe 43 is known per se. The regulating module 42 and the temperature probe 43 are for example positioned inside the protective casing 38.

The diffracting particles 22 are for example biological particles, i.e. cells (for example endothelial cells, neurones, tumoral cells), bacteria or bacterial colonies, cells or cell aggregates.

The diffracting particles 22 preferably have a diameter of less than 20 µm. The diameter of the diffracting particles 22 is for example comprised between 1 µm and 100 µm. The cells have a diameter of the order of 10 µm.

The liquid medium 24 is delimited by the transparent surface 29, visible in FIG. 3. The diffracting particles 22 are immersed in the liquid medium 24, certain particles 22 being in contact with said transparent surface 29.

The medium 24 is positioned between the light source 26 and the photodetector array 28 and is substantially perpendicular to the vertical direction Z corresponding to the illumination direction of the medium by the light source 26, as illustrated in FIG. 3.

The light source 26 is able to emit a light beam 44 in the vertical direction Z, in order to illuminate the liquid medium 24 comprising the diffracting particles 22.

The light source 26 is positioned at a first distance D1 from the transparent surface 29 in the vertical direction Z. The first distance D1 preferably has a value comprised between 1 cm and 30 cm, for example equal to 8 cm.

The light source 26 is a spatially coherent source. The light source 26 for example includes, a point-like source such as a light-emitting diode 46, also called a LED (Light-Emitting Diode), and a diaphragm 48 positioned in contact with the LED 46, as illustrated in FIG. 3. The diaphragm 48 has a diameter comprised between 50 µm and 500 µm, preferably substantially equal to 100 µm, and is placed in contact with the light source 26. This gives the possibility of increasing the spatial coherence of the light radiation. Alternatively, the light source 26 consists of the light-emitting diode 46, and does not include any diaphragm. The light-emitting diode 46 then has sufficiently reduced dimensions so as to be considered as spatially coherent, the diameter of the light-emitting diode 46 being less than one-tenth of the first distance D1.

Still alternatively, the light source 26 is a source of spatially and temporarily coherent light, for example a laser diode (DL) or further a laser diode of the VCSEL type (Vertical Cavity Surface Emitting Laser).

The photodetector array 28 is able to acquire images of the radiation transmitted through the medium 24 containing the diffracting particles 22 illuminated by the light beam 44. By transmitted radiation is meant the radiation crossing the medium 24 so that the photodetector array 28 and the light source 26 are located on either side of the medium 24 and of the diffracting particles 22.

The photodetector array 28 is a two-dimensional image sensor, i.e. in a plane perpendicular to the vertical axis Z. The photodetector array 28 is a pixelized image sensor, for example a CMOS sensor. Alternatively, the photodetector array 28 is a CCD (Charged-Coupled Device) sensor.

The photodetector array 28 includes a plurality of pixels, not shown. Each pixel of the photodetector 28 has dimensions of less than or equal to 10 µm.

The photodetector array 28 additionally includes microlenses, not shown, each microlens being positioned above a corresponding pixel. Such microlenses are integrated to the sensor. They give the possibility of improving the collection yield and do not form magnifying optics positioned between the transparent surface 29 and the photodetector 28. The images acquired by the photodetector array 28 are formed with the radiation directly transmitted through the illuminated medium 24, in the absence of any magnifying optics positioned between the transparent surface 29 and the photodetector array 28. The photodetector 28 is then called a lensless imaging device, and is able to form an image of the medium 24, while being placed at a small distance from the latter. By small distance, is meant, as indicated earlier, a distance of less than a few centimeters, preferably less than 1 cm, or even less than 1 mm, the second distance D2 for example being equal to 700 µm.

Figure 5:
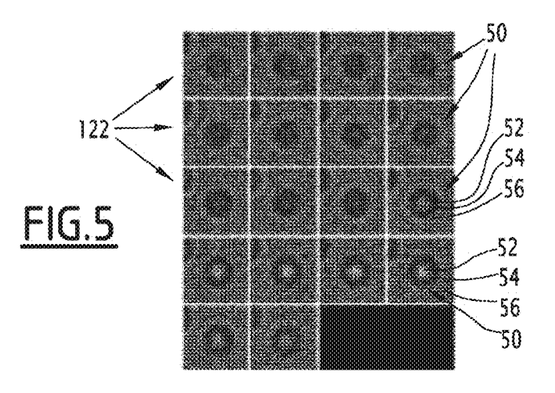
FIG. 5 is a set of images, each containing a diffraction pattern corresponding to a same particle, the images being acquired via the photodetector of FIG. 3, during a time period of 3 hours, during the adhesion of the particle to the transparent surface.
Figure 11:
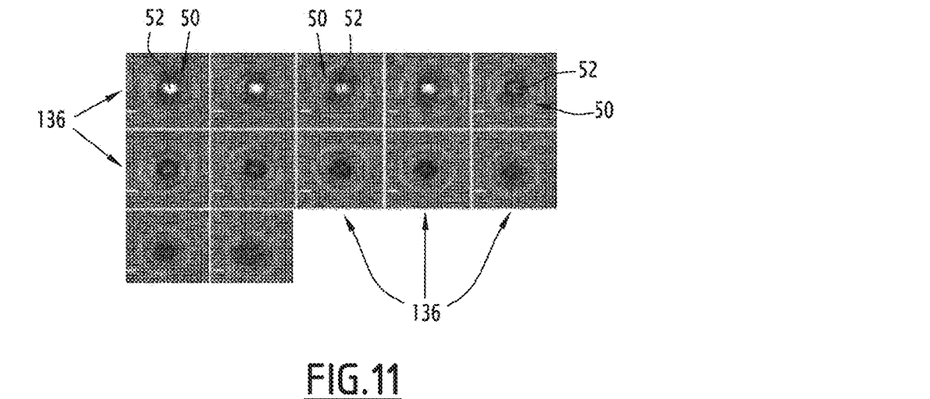
FIG. 11 is a view similar to that of FIG. 5 upon detachment of the particle relatively to the transparent surface, during a time period of 100 minutes.

The photodetector array 28 is then able to measure the intensity I of at least one elementary diffraction pattern 50 transmitted through the medium 24, each elementary diffraction pattern 50, visible in FIGS. 5 and 11, corresponding to waves diffracted by one diffracting particle 22, during the illumination of the medium 24. Thus, the photodetector array gives the possibility of obtaining an image $I_1$, a so-called observed image, including one or several elementary diffraction patterns 50. The intensity I is for example expressed in gray levels, the gray level value being comprised between 0 and 256 in the example of FIGS. 6, 7 and 12. In other words, the gray level value is expressed on 8 bits in this example. Alternatively, the gray level value is expressed on a number of bits different from 8, such as 12 bits, 14 bits, or further 16 bits.

The photodetector 28 is positioned at a second distance D2 from the transparent surface 29 along the vertical direction Z. The second distance D2 has a value comprised between 100 µm and a few centimeters, preferably less than 1 cm, and still preferably comprised between 100 µm and 2 mm. In the described example, the second distance D2 is equal to 700 µm.

By preferring a second distance D2 of a small value, i.e. a short distance between the photodetector array 28 and the transparent surface 29, it is possible to limit the interference phenomena between different diffraction patterns when the medium 24 is illuminated.

The transparent surface 29 for example is in the form of a transparent slide, having a thickness substantially equal to 170 µm along the vertical direction Z. As an optional addition, a deposit of a substance, promoting adhesion of the cells, such as fibronectin, is applied on the transparent surface 29, although this is not indispensable.

The first computing software 36 is able to compute, from at least one image acquired by the photodetector 28 and for at least one particle 22, the primary indicator characterizing the state of adhesion of the particle 22 to the transparent surface 29, from each elementary diffraction pattern 50.

The computed primary indicator is for example dependent on the intensity I at the center 52 of an elementary diffraction pattern 50. The inventors actually noticed surprisingly that the intensity I at the center 52 of an elementary diffraction pattern 50 varies according to the state of the adhesion at the transparent surface 29 of the corresponding particle 22 to this diffraction pattern 50, as illustrated in FIG. 5. The inventors in particular have observed that the intensity I at the center 52 of the diffraction pattern increases when the particle 22 adheres to the transparent surface 29.

In the example of FIG. 5, each diffraction pattern 50 includes the center 52, also called a central area, a first ring 54 which is darker than the center 52 and a second brighter ring 56 than the first ring 54. Generally, each elementary diffraction pattern 50 includes several concentric rings 54, 56, of a circular or elliptical shape depending on the nature of the observed particle. These rings extend around a central area 52.

The computed primary indicator is for example a ratio R of the intensity of the center 52 divided by the intensity of the second ring 56. The term of «center» designates an area of interest at the center of the diffraction pattern, including one or several pixel for which the gray level is homogenous. The particle 22 is then considered as having adhered to the transparent surface 22, the associated state of adhesion being equal to «adhered», when the value of the ratio R is greater than or equal to a first predetermined threshold S1. The first threshold S1 is for example equal to 1.25. By complementarity, when the value of the ratio R is less than the first threshold S1, the particle 22 is considered as being separate from the transparent surface 22, the associated state of adhesion being equal to "detached". The first threshold S1 may be adjusted during experimental tests.

Alternatively, the computed primary indicator is equal to the maximum intensity Imax of the center 52 of the diffraction pattern 50, and the particle 22 is considered as having adhered to the transparent surface 22 when the value of said maximum intensity Imax of the center 52 is greater than or equal to a second predetermined threshold S2. The second threshold S2 is for example equal to 100 when the value of the gray level is comprised between 0 and 256. Generally, the second threshold S2 is for example substantially equal to two-fifths of the measurement dynamics. In other words, for a maximum intensity value measured on 12 bits, the maximum value of the interval of values is equal to 4,096 and the second threshold is then substantially equal to 1,638.

The determination of the center 52 of an elementary diffraction pattern 50 is for example carried out manually, the operator performing a manual selection of the relevant area of the image as being representative of the central area of a diffraction pattern. The primary indicator is then determined according to the determined center 52.

Moreover, when the number of cells is high, it is possible to establish a reference elementary diffraction pattern, corresponding to a cell having adhered, i.e. including a central area for which the average intensity is greater than a predetermined value. The application of an autocorrelation function gives the possibility of identifying the localization of the centers of each elementary diffraction pattern having identical characteristics. The application of such an algorithm gives the possibility of automatically counting the number of adherent cells from among a population of cells.

An exemplary algorithm is the following.

If $I_1(x,y)$ and $I_2(i,j)$ respectively refer to the observed image and to a reference elementary diffraction pattern, the application of an autocorrelation function, preferably normalized, leads to a correlation image $I_3(x,y)$ such that $$I_3(x, y) = \frac{\sum_{i,j} I_2(i, j) \times I_1(x+i, y+j)}{\sqrt{\sum_{i,j} I_2^2(i, j) \sum_{i,j} I_1^2(x+i, y+j)}} \quad (1)$$

In this image $I_3$, each intensity peak in the correlation image $I_3$ corresponds to the position of the center of the diffraction pattern corresponding to the reference image $I_2$.

The number and the position of the adherent cells in the observed image $I_1$ are then obtained.

In other words, the intensity $I_3(x,y)$ of each pixel of the correlation image is for example considered as a primary indicator, the value of which is dependent on the state of adhesion of a cell generating an elementary diffraction pattern 50 centered on this pixel (x, y). After suitable threshold setting, only showing the pixels for which the intensity $I_3(x, y)$ exceeds a certain threshold, only appear the pixels corresponding to the center of a diffraction pattern 50 generated by an adherent cell.

Additionally or alternatively, it is possible to establish a reference diffraction pattern $I_2'$, corresponding to a cell not having adhered, i.e. including a central area, for which the average intensity is less than a predetermined value. The application of an autocorrelation function, as described earlier via equation (1), gives the possibility of obtaining a correlation image $I_3'$, the latter giving the possibility of counting and localizing the non-adherent cells in the observed image $I_1$. The application of such an algorithm gives the possibility of automatically counting the number of non-adherent cells from among a population of cells. It also allows localization of these cells in the observation image $I_2'$ obtained with the device.

By simultaneously applying both algorithms described earlier, it is possible to establish a percentage of adherent or non-adherent cells with respect to the whole of the cells.

According to an alternative, a plurality of reference diffraction patterns $I_2$, $I_2'$, $I_2''$ are available corresponding to different states of a cell: an adherent cell, a non-adherent cell, a cell being adhered thereto, the central portion of each reference pattern $I_2$, $I_2'$, $I_2''$ differing according to the state of adhesion of the cell. The autocorrelation algorithm applied gives the possibility of obtaining as many correlation images $I_3$, $I_3'$, $I_3''$ as there are reference patterns. This gives the possibility of identifying each elementary diffraction pattern 50 for which the pattern is close to a relevant reference elementary pattern $I_2$, $I_2'$, $I_2''$. This also gives the possibility of determining the coordinates of the center of each thereby identified elementary diffraction pattern 50.

Thus, the comparison of the observed image 11 with one or several reference elementary diffraction patterns $I_2$, $I_2'$, $I_2''$ gives the possibility of counting and localizing the whole of the cells observed on the image $I_1$. From the coordinates, in the image $I_1$, of the center of each thereby identified diffraction pattern, a region of interest is for example defined around this center, to which is applied the primary indicator described earlier. The region of interest typically comprises from 10 to 1,000 pixels, preferably from 10 to 100 pixels. The application of the primary indicator allows identification of the adherent cells from among the whole of the detected cells.

Alternatively, in order to detect the center 52 of the diffraction pattern, the first computing software 36 is able to reconstruct an image of the diffracting particles from the image acquired by the photodetector 28, and according to a known holographic reconstruction algorithm. Such an algorithm allows, from an elementary diffraction pattern, reconstruction of the geometry and/or of the position of the diffracting object. The first computing software 36 is then able to detect in the reconstructed image the position corresponding to the center 52 of each diffraction pattern, and then of determining a region of the image acquired by the photodetector 28, this region including the corresponding diffraction pattern 50. The first computing software 36 is then able to detect the center 52 of the diffraction pattern by a match with the detected position in the reconstructed image.

The second computing software 37 is able to compute, from at least one image acquired by the photodetector 28 and for at least one particle 22, at least one secondary indicator S, K characterizing the spreading of a cell 22 having adhered to the transparent surface 29, each secondary indicator S, K being distinct from the primary indicator.

At least one computed secondary indicator S, K preferably depends on a moment of order M of the distribution X of the intensity I of a corresponding elementary diffraction pattern 50, M being an integer with a value greater than or equal to 3.

The second computing software 37 is for example able to compute a first secondary indicator S depending on the moment of order 3 of the intensity at the center 52 of the corresponding diffraction pattern. The second computing software 37 is also able to compute a second secondary indicator K depending on the moment of order 4 of said intensity at the center 52 of the diffraction pattern.

The second computing software 37 is further able to compute a time derivative of at least one secondary indicator for detecting the beginning of the spreading of the cell 22 having adhered to the transparent surface 29 (cell spreading).

The spreading of the cell 22 corresponds to a change in shape of the cell, the latter being initially of a round shape when it is immersed in the liquid medium 24 or further when it comes into contact with the transparent surface 29. After this change in shape which occurs after a certain adhesion period of the cell 22 to the surface 29, the cell 22 assumes a well distinct shape which varies according to the cell line, the cell 22 then being for example of an oblong shape or further a triangular shape.

The second computing software 37 is, similarly to the first computing software 36, able to determine a region of the acquired image including the corresponding diffraction pattern 50.

The first secondary indicator S then verifies the following equation:

$$S = E\left[\left(\frac{X-\mu}{\sigma}\right)^3\right] \quad (2)$$

where X represents the distribution of the intensity I of the determined region of the acquired image including the elementary diffraction pattern 50, μ represents the quadratic average of the intensity of said determined region, and σ represents the standard-deviation of the intensity of said determined region.

The second secondary indicator K verifies the following equation:

$$K = E\left[\left(\frac{X-\mu}{\sigma}\right)^4\right] \quad (3)$$

where the parameters X, μ and σ are identical with those of the preceding equation (2).

The protective casing 38 is for example with the shape of a cylinder, as illustrated in FIGS. 1 and 2. The protective casing 38 has a height H along the vertical direction Z and a radius R along a radial direction perpendicular to the vertical direction Z. The height H and the radius R of the casing 38 are for example in centimeters.

The light-emitting diode 46 is for example monochromatic with a pass band with the width for example comprised between 20 nm and 60 nm, preferably equal to 40 nm. The light-emitting diode 46 for example has an emission wavelength comprised between 500 nm and 520 nm and a power of the order of one Watt.

Figure 4:
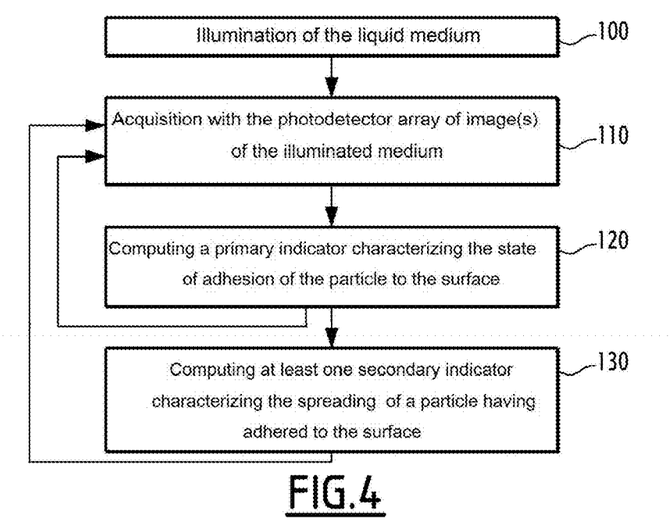

The operation of the characterization system 20 according to the invention will now be described in view of FIG. 4 illustrating a flow chart of the characterization method according to the invention.

During the initial step 100, the liquid medium 24 is illuminated with the spatially coherent light source 26, the light beam 44 being directed along the vertical direction Z.

During step 110, the photodetector array 20 carries out the sequential acquisition of several transmission images $I_n(x, y)$, $I_{n+m}(x,y)$ at different instants n and n+m. Each transmission image $I_n(x,y)$, $I_{n+m}(x,y)$ is formed by the transmitted radiation, at the corresponding acquisition instant, by the illuminated liquid medium 24. In other words, the photodetector array 28 measures the intensity I of the elementary diffraction patterns transmitted by the cells immersed in the illuminated medium 24, each elementary diffraction pattern corresponding to waves diffracted by the diffracting particles 22 during the illumination of the medium 24, these diffracted waves interfering with the incident wave.

The images $I_n(x,y)$, $I_{n+m}(x,y)$ are for example acquired every second in order to be able to carry out a tracking of the particles 22, via a method for tracking cells (cell tracking) which for example consists of pairing the closest particles in two successive images. Such a method for tracking cells is for example described in the article "Automated tracking of migrating cells in phase-contrast videomicroscopy sequences using image registration" of Hand A. J.; Sun T.; Barber D. C.; Hose D. R, MacNeil S., published in the journal: Journal of Microscopy in 2009, Volume 234, on pages 62 to 79.

The acquired images taken into account for computing the primary indicator or further for computing the secondary indicators S, K, are for example spaced out in time by one or a few tens of minutes.

The observation of an utilizable diffraction pattern, by placing the photodetector array 28 at a such small distance is notably due to the absence of any magnifying optics between the liquid medium 24 and the photodetector 28.

During the acquisition step 110, the photodetector 28 is positioned at a small distance from the liquid medium 24, the second distance D2 between the liquid medium 24 and the photodetector 28 along the vertical direction Z being of the order of a few millimeters, and preferably less than 1 cm, or even 1 mm.

At the end of the acquisition step 110, the first computing software 36 begins, during step 120, with determining a region of the acquired image $I_n(x, y)$ which includes a diffraction pattern 50 by comparing the acquired image $I_n(x,y)$ with one or several reference elementary patterns $I_2$, $I_2'$, $I_2''$ . . . , as explained in the preceding embodiment. This comparison gives the possibility of identifying each elementary diffraction pattern 50, for which the pattern is close to a relevant reference elementary pattern $I_2$, $I_2'$, $I_2''$. It also allows determination of the coordinates of the center of each thereby identified elementary diffraction pattern. The comparison between the acquired image and each reference elementary pattern $I_2$, $I_2'$, $I_2''$ for example consists in a normalized autocorrelation between said acquired image and said reference region. The result of this is one or several correlation images $I_3$, $I_3'$, $I_3''$, each intensity peak of which corresponds to the center of an elementary pattern 50, the pattern of which corresponds to the relevant reference elementary pattern $I_2$, $I_2'$, $I_2''$.

Thus, the comparison of the observed image $I_1$ with one or several reference elementary diffraction patterns $I_2$, $I_2'$, $I_2''$ gives the possibility of counting and of localizing the whole of the cells observed on the image $I_1$.

From the coordinates, in the image $I_1$, of the center of each thereby identified diffraction pattern, it is possible to define a region of interest around this center, to which the secondary indicator mentioned earlier is applied. The application of the secondary indicator requires a more extended region of interest when the primary indicator is applied. For example, the area of interest is a square of 40×40 pixels.

Alternatively, the identification of each reference elementary pattern on the image $I_1$ is performed manually, as well as the selection of a region of interest corresponding to each thereby identified elementary pattern.

FIG. 5 illustrates a plurality of thereby determined regions of interest 122 for a same particle 22 from images acquired every 10 minutes, said particle 22 being tracked via the tracking method described earlier. Each determined region 122 includes the diffraction pattern 50 associated with said particle 22.

Alternatively, in order to detect the center 52 of the diffraction pattern, the first computing software 36 reconstructs an image of the particles 22 from the acquired image $I_n(x,y)$ by the photodetector 28, and according to a known holographic reconstruction algorithm allowing, from an elementary diffraction pattern 50, the reconstruction of the geometry and/or the position of the diffracting object. The reconstruction algorithm is for example described on page 10, line 7 to page 11, line 3 of the application FR 12 56816 filed on Jul. 13, 2012 by the applicant of the present application. The first computing software 36 is then able to detect in the reconstructed image the position corresponding to the center 52 of each diffraction pattern, and then of determining a region of the image acquired by the photodetector 28, this region including the corresponding diffraction pattern 50. The first computing software 36 is finally able to detect the center 52 of the diffraction pattern by matching with the position detected in the reconstructed image. In a similar way to what was described earlier, the thereby determined region is then a region of interest, with predefined shape and size, for example a square with a side of 40 pixels, positioned around the detected position of the center 52 of the diffraction pattern.

The first computing software 36 then calculates the primary indicator, the latter for example being the maximum intensity Imax of the center 52 of the diffraction pattern, and the particle 22 is considered as having adhered to the transparent surface 22 when the value of said maximum intensity Imax of the center 52 is greater than or equal to the second predetermined threshold S2.

Figure 6:
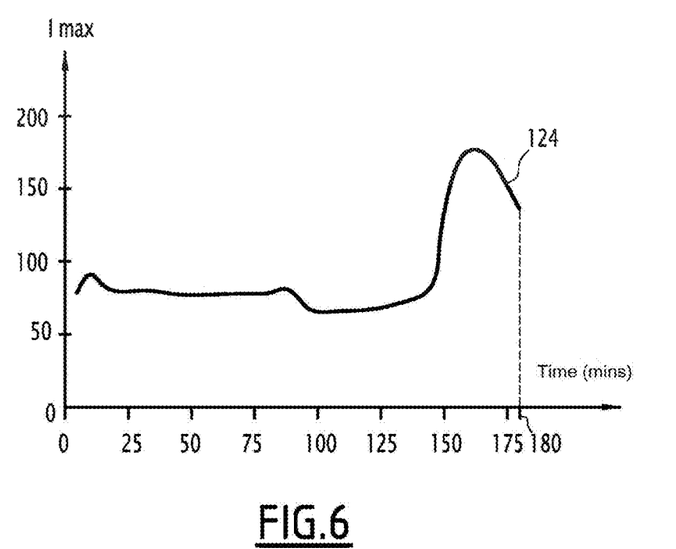
FIG. 6 is a curve representing, versus time on a period of 3 hours, a primary indicator characterizing the state of adhesion to the transparent surface of the particle associated with the successive images of FIG. 5.

In the example of FIG. 6, a curve 124 represents the time-dependent change in the maximum intensity Imax in the regions of interest 122 determined overtime, and the adhesion of the particle 22 corresponds to a time instant slightly less than 150 minutes, the second threshold S2 being substantially equal to 100. It is recalled that each region of interest extends around the center of an elementary diffraction pattern 50 of the observed image $I_1$. The method then gives the possibility of establishing adhesion kinetics. Alternatively, the first computing software 36 calculates the primary indicator as the ratio R of the intensity of the center 52 divided by the intensity of the second ring 56. The particle 22 is then considered as having adhered to the transparent surface 22, the associated state of adhesion being equal to "adhered" state, when the value of the ratio R is greater than or equal to the first predetermined threshold S1. The value of the intensity of the second ring may easily be evaluated by producing a profile of the region of interest, or by selecting a reduced additional area of interest, limited to a portion of the second ring, and by determining the average intensity level of this reduced additional area of interest.

Figure 7:
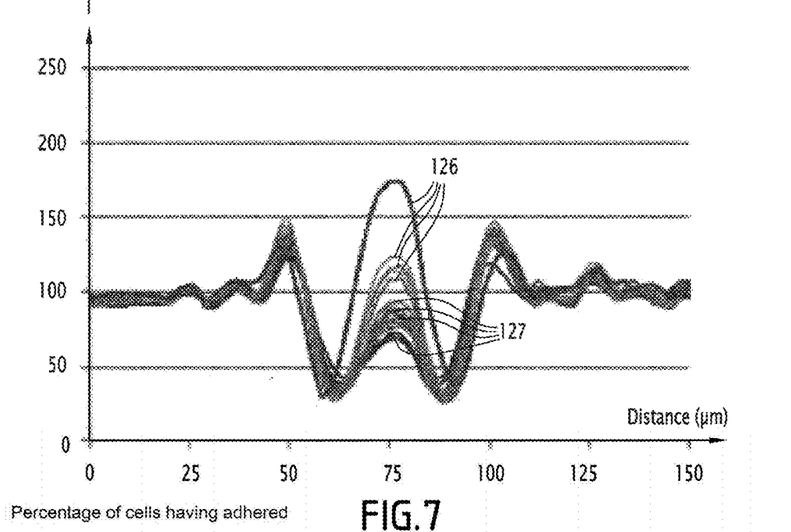
FIG. 7 is a set of 19 curves associated with different successive images during a time period of 3 hours, each image containing a diffraction pattern corresponding to a same particle, two successive curves being separated by an interval of 10 minutes, each curve representing the intensity in the vicinity of the center of the diffraction pattern versus a distance expressed in micrometers, the center of the diffraction pattern corresponding to the distance equal to 75 µm.

In the example of FIG. 7, several horizontal profiles 126, 127 correspond to the regions 122 illustrated in FIG. 5. Each profile represents the intensity on a horizontal line passing through the center of the image to which it relates, the center 52 of the corresponding diffraction pattern corresponding to the coordinate 75 µm. Each determined region 122 taken into account contains the elementary diffraction pattern 50 corresponding to the same particle 22, said particle 22 being tracked via the tracking method as described earlier. The time-dependent change in the diffraction pattern 50 produced by the particle 22 is then available. The second ring 56 is substantially centered on the center 52, and corresponds to the coordinates substantially equal to 50 µm and 100 µm in FIG. 7. In other words, in the example of FIG. 7, the second ring 56 has a radius of about 25 µm.

In FIG. 7, a set of first curves 126 is observed for which the intensity in the vicinity of the center 52, i.e. the intensity around the coordinate 75 µm, is greater than the second threshold S2 on the one hand, and a set of second curves 127 is observed for which the intensity in the vicinity of the center 52 is less than the second threshold S2. This threshold S2 is here equal to 100. For the first curves 126, the value of the ratio R is also greater than a first threshold S1, and for the second curves 127 the value of the ratio R is less than the first threshold S1. In other words, the first curves 126 correspond to the time period during which the corresponding particle 22 adheres to the surface 29, and the second curves 127 correspond to the time period during which the corresponding particle 22 is at the distance from said surface 29.

Figure 8:
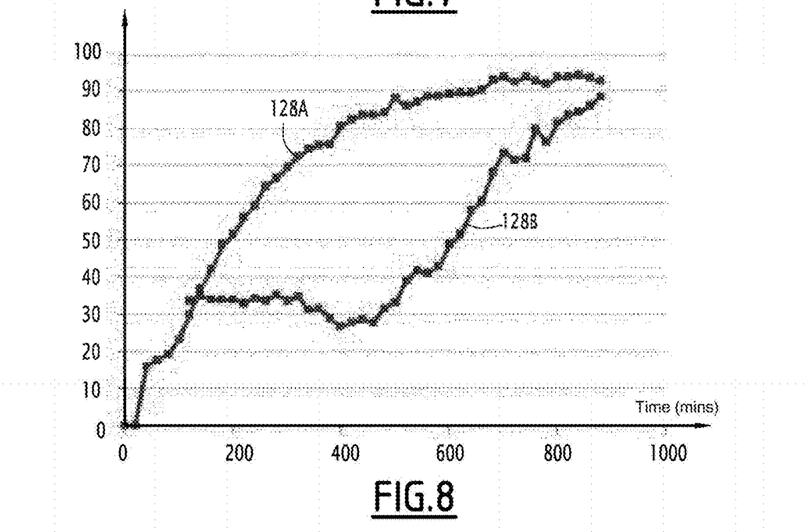
FIG. 8 is a set of two curves each representing versus time, a percentage of cells having adhered to the transparent surface, each curve being associated with a respective population of cells.

The characterization method according to the invention then allows determination, overtime, and via the primary indicator, of a percentage of particles 22, such as cells, having adhered to the transparent surface 29, as illustrated in FIG. 8. It is then possible to characterize a first population of cells 22 with respect to a second population of cells 22 by comparing the adhesion rate to the transparent surface 29 of the cells 22 of each of the populations. As an example in FIG. 8, a first curve 128A and a second curve 128B each illustrate overtime, the percentage of cells 22 having adhered to the transparent surface 29, the first curve 128A being associated with the first population for which the percentage of cells having adhered increases more rapidly than the one corresponding to the second population associated with the second curve 128B.

The step for computing the primary indicator 120 is applied by the characterization system 20 with a periodicity for example of the order of 10 minutes, and the characterization system 20 returns to the acquisition step 110 at the end of each computing step 120, or else passes to the computing step 130 of at least one secondary indicator characterizing the spreading of the cell 22 when for example the state of adhesion for said particle is equal to "adhered".

During step 130, the second computing software 37 then computes, from at least one image $I_n(x, y)$ acquired by the photodetector 28 and for at least one particle 22, at least one secondary indicator S, K characterizing the spreading of the cell 22 having adhered to the transparent surface 29.

The second computing software 37 for example begins by computing the first secondary indicator S versus the moment of order 3 of the intensity at the center 52 of the corresponding diffraction pattern, preferably with equation (2).

The acquired region of the image including the diffraction pattern 50 is determined in a similar way to what was described earlier for the computing step 120. During the preceding step 120, the regions 122 determined for a given particle 22 are preferably stored in the memory 34 of the information processing unit in order to be used for computing the secondary indicators S, K during the next step 130. Alternatively, the second computing software 37 again determines said regions of the acquired image including the diffraction patterns 50.

The second computing software 37 then computes the second secondary indicator K versus the moment of order 4 of said intensity at the center 52 of the corresponding diffraction pattern, preferably with equation (3).

Figure 9:
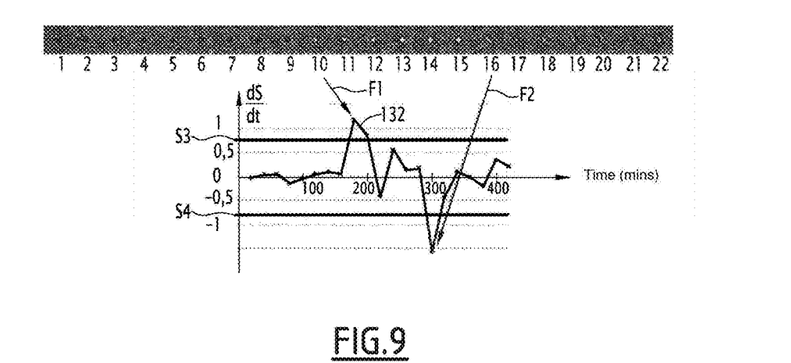
FIG. 9 is a curve each illustrating the time-dependent change over time of the time derivative of a first secondary indicator characterizing the spreading of a cell having adhered to the transparent surface, the first secondary indicator depending on the moment of order 3 of the intensity at the center of the diffraction pattern corresponding to said cell.
Figure 10:
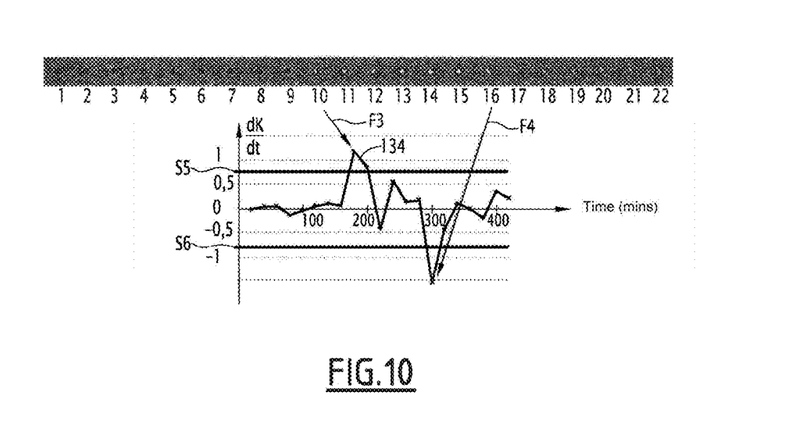
FIG. 10 is a curve illustrating the time-dependent change, versus time, of the time derivative of a second secondary indicator characterizing the spreading of the cell having adhered to the transparent surface, the second secondary indicator depending on the moment of order 4 of the intensity at the center of the diffraction pattern corresponding to said cell.

Additionally, the second computing software 37 the computes the time derivative of one or of each of the secondary indicators S, K in order to determine a beginning of the spreading of the cell 22 having adhered to the transparent surface 29, as illustrated in FIGS. 9 and 10.

The inventors then noticed that the exceedance of a third threshold S3 by the time derivative dS/dt of the first secondary indicator S corresponds to the adhesion of the particle 22 to the transparent surface 29, as this is visible in FIG. 9 wherein the curve 132 illustrates said time derivative dS/dt of the first secondary indicator. The exceedance of the third threshold S3 actually corresponds to the transition from the numbered region 9 to the region numbered 10 (arrow F1), this transition itself corresponding to the adhesion of the particle 22 to the surface 29. In the example of FIG. 9, the value of the third threshold S3 is substantially equal to 0.75.

The moment when the time derivative dS/dt of the first secondary indicator is then less than a fourth threshold S4 corresponds to the beginning of the spreading of the observed cell 22, i.e. to the change in the shape of the cell having adhered to the surface 29 in the case when the particle 22 is a cell. In FIG. 9, the crossing of the fourth threshold S4 corresponds to the transition from the region numbered 15 to the region numbered 16 (arrow F2), this transition itself corresponding to a change in shape of the diffraction pattern 50, which expresses the change in shape of the cell 22 having adhered to the surface 29. In the example of FIG. 9, the value of the fourth threshold S4 is substantially equal to −0.75.

Similarly, the inventors noticed that the exceedance of a fifth threshold S5 by the time derivative dS/dt of the second secondary indicator K corresponds to the adhesion of the particle 22 to the transparent surface 29, as this is visible in FIG. 10 wherein the curve 134 illustrates said time derivative dK/dt of the second secondary indicator. The exceedance of the fifth threshold S5 corresponds to the transition from the region numbered 9 to the region numbered 10 (arrow F3) in FIG. 10, this transition itself corresponding to the adhesion of the particle 22 to the surface 29. In the example of FIG. 10, the value of the fifth threshold S5 is substantially equal to 0.75.

The moment when the time derivative dK/dt of the second secondary indicator is then less than a sixth threshold S6, also corresponds to the beginning of the spreading of the cell 22 observed. In FIG. 10, the crossing of the sixth threshold S6 corresponds to the transition from the region numbered 15 to the region numbered 16 (arrow F4), this transition itself corresponding to the change in the shape of the diffraction pattern 50, which expresses the change in the shape of the cell 22 having adhered to the surface 29. In the example of FIG. 10, the value of the sixth threshold S6 is substantially equal to −0.75.

The step 130 for computing the secondary indicators S, K is applied by the characterization system 20 with a periodicity for example of the order of 20 minutes, and the characterization system 20 returns to the acquisition step 110 at the end of each computing step 130.

One skilled in the art will understand that the computing steps 120, 130 are carried out successively as this is illustrated in FIG. 4, or else are carried out in parallel with each other from acquired images during step 110.

The characterization method and the characterization system 20 according to the invention then give the possibility of characterizing the adhesion of a given particle 22 to the transparent surface 29, and if necessary further characterizing the spreading of the cell 22 having adhered to the transparent surface 29, as this was described earlier notably with reference to FIGS. 5 to 10.

Figure 12:
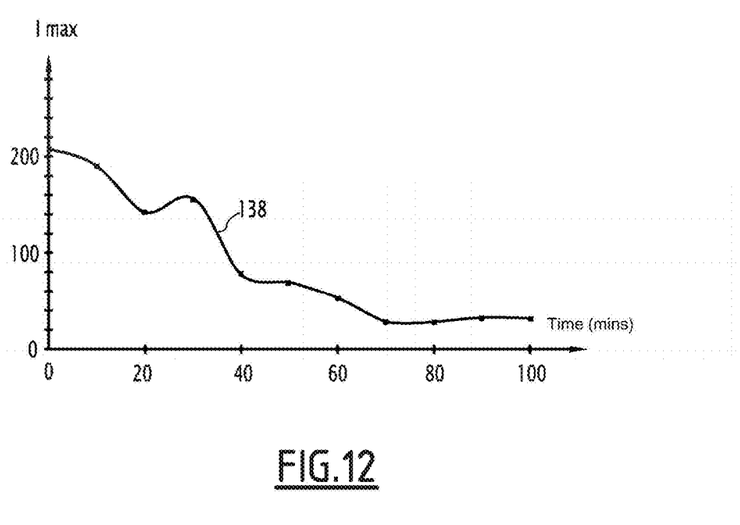
FIG. 12 is a curve similar to the one of FIG. 6 characterizing the state of adhesion of the particle associated with the images of FIG. 11.

Additionally, and complementarily, the characterization method and the characterization system 20 according to the invention also allow characterization of the detachment of the particle 22 having adhered to the transparent surface 29, as illustrated in FIGS. 11 and 12. The detachment of the particle 22 corresponds to lack of adhesion of said particle to the surface 29 subsequently to a time period during which the particle 22 has adhered to the transparent surface 29. This detachment is characterized with the primary indicator, the value of the state of adhesion then passing for said particle 22 from the "adhered" state to the «detached» state.

FIG. 11 is a view similar to the one of FIG. 5 during the detachment of the particle 22 with respect to the transparent surface 29, FIG. 11 illustrating a plurality of regions 136 determined every 10 minutes during a time period of 100 minutes, the determination of the regions 136 being similar to what was described earlier for the computing step 120.

In FIG. 11, it is observed that the intensity I at the center 52 of the diffraction pattern is high at the beginning of the time period when the particle 22 is still adhered to the surface 29, and then that this intensity decreases over time. This is for example expressed by lowering of the maximum intensity Imax at the center 52 of the diffraction pattern which then becomes less than the second threshold S2, which indicates that the state of adhesion is then equal to the "detached" state, and in other words that the particle 22 is detached from the surface 29, as illustrated in FIG. 12.

In the example of FIG. 12, a curve 138 illustrates the time-dependent change in the maximum intensity Imax in the regions 136 determined overtime, and the detachment of the particle 22 corresponds to a time instant slightly less than 40 minutes, the second threshold S2 being substantially equal to 100 in this example. This instant corresponds to the transition between the fourth determined region 136 and the fifth determined region 136 in FIG. 11, a transition for which a significant decrease in the intensity at the center 52 of the diffraction pattern is observed.

The characterization system 20 according to the invention is then able to characterize the adhesion of the particle 22 to the transparent surface 29 when said particle 22 moves towards this surface, but also the detachment of a particle 22 with respect to the surface 29 to which the particle was adhered beforehand.

The characterization system 20 according to the invention further allows detection of the spreading of the cell 22 which corresponds to a change in the shape of the cell, the latter being initially of a round shape and then assuming, after a certain period of adhesion to the surface 29, a well distinct shape which varies according to the cell line, the cell 22 then for example being of an oblong shape, or further of a triangular shape.

The characterization system 20 according to the invention is particularly inexpensive, since the light source 26 is for example formed with a simple light-emitting diode 46 coupled with a diaphragm 48 and that the photodetector array 28 is a standard sensor of the CMOS or CCD type which does not require having a high resolution.

The characterization system 20 according to the invention further has particularly reduced size, the dimensions of the protective casing 38 being centimetric dimensions.

The characterization system 20 according to the invention is further very easy to apply, as this was described earlier, the adhesion or the detachment of a given particle 22 being characterized via the sole primary indicator, the spreading of the cell 22 having adhered to the surface 29 being able to be characterized via only one of the two secondary indicators S, K.

Thus it is conceivable that the characterization method and the characterization system 20 according to the invention are less expensive and easier to apply.

The invention claimed is:

1. A method for characterizing a state of adhesion of at least one particle, via a system comprising a spatially coherent light source and a photodetector array, the particle(s) being contained in a liquid medium, the liquid medium being delimited by a transparent surface, the particle(s) being able to adhere to said transparent surface,
the method comprising:
    illuminating the medium with the spatially coherent light source,
    acquiring at least one image by the photodetector array, the image being formed by radiation transmitted by the illuminated medium and including at least one elementary diffraction pattern, each elementary diffraction pattern corresponding to waves diffracted by a particle during the illumination of the medium,
    computing, from at least one acquired image and for at least one particle, a primary indicator characterizing the state of adhesion of the particle to the transparent surface, and
    computing, from at least one acquired image and for at least one particle, at least one secondary indicator characterizing the spreading of a cell having adhered to the transparent surface, each secondary indicator being distinct from the primary indicator.

2. The method according to claim 1, wherein the photodetector array is able to measure the intensity of at least one diffraction pattern, and
    wherein the computed primary indicator depends on the intensity at the center of a corresponding diffraction pattern.

3. The method according to claim 2, wherein a particle is determined as being adherent when the value of said primary indicator exceeds a threshold.

4. The method according to claim 1, wherein computing each primary indicator includes the localization on the acquired image, of the center of each elementary diffraction pattern corresponding to a predetermined pattern.

5. The method according to claim 1, wherein computing each primary indicator includes the localization, on the acquired image, of the center of an elementary diffraction pattern, this localization being achieved from:

a reconstruction of an image of the particle associated with said elementary diffraction pattern, by applying a reconstruction algorithm, and then the detection in the reconstructed image, of the position corresponding to the center of said elementary diffraction pattern.

6. The method according to claim 4, wherein the method further comprises the definition of a region of interest around the center of each elementary diffraction pattern.

7. The method according to claim 1, wherein the photodetector array is able to measure the distribution of the intensity of at least one diffraction pattern, and wherein at least one computed secondary indicator depends on a moment of order M of the intensity at the center of a corresponding diffraction pattern, M being an integer with a value greater than or equal to 3.

8. The method according to claim 7, wherein the method further comprises computing the time derivative of at least one computed secondary indicator for detecting the spreading of the cell having adhered to the transparent surface.

9. The method according to claim 7, wherein a first computed secondary indicator depends on the moment of order 3 of the intensity at the center of the corresponding diffraction pattern.

10. The method according to claim 9, wherein computing each first secondary indicator includes the determination of a region of interest of the acquired image including the corresponding diffraction pattern, and each first secondary indicator verifies the following equation:

$$S = E\left[\left(\frac{X-\mu}{\sigma}\right)^3\right]$$

where X represents the distribution of the intensity of said determined region of interest, $\mu$ represents the quadratic average of the intensity of the determined region, and $\sigma$ represents the standard-deviation of the intensity of the determined region.

11. The method according to claim 7, wherein a second computed secondary indicator depends on the moment of order 4 of the intensity at the center of the corresponding region of interest.

12. The method according to claim 11, wherein computing each second secondary indicator includes the determination of a region of the acquired image including the corresponding diffraction pattern, and each second secondary indicator verifies the following equation:

$$K = E\left[\left(\frac{X-\mu}{\sigma}\right)^4\right]$$

where X represents the distribution of the intensity of said determined region of interest, $\mu$ represents the quadratic average of the intensity of the determined region of interest, and $\sigma$ represents the standard-deviation of the intensity of the determined region of interest.

13. A system for characterizing a state of adhesion of at least one particle, the particle(s) being contained in a liquid medium, the liquid medium being delimited by a transparent surface, the particle(s) being able to adhere to said transparent surface, the system comprising:

a source of spatially coherent light able to emit a light beam for illuminating the liquid medium, a photodetector array able to acquire at least one image of radiation transmitted by the illuminated medium, the image including at least one diffraction pattern, each diffraction pattern corresponding to waves diffracted by a particle of the illuminated medium, and a data processor and a memory storing a first program configured to compute, from at least one acquired image and for at least one particle, a primary indicator characterizing the state of adhesion of the particle to the transparent surface and a second program configured to compute, from at least one acquired image and for at least one particle, at least one secondary indicator characterizing the spreading of a cell having adhered to the transparent surface, each secondary indicator being distinct from the primary indicator.

* * * * *